(12) United States Patent
Hassan (10) Patent No.: US 6,680,308 B1
(45) Date of Patent: Jan. 20, 2004

(54) USE OF ORGANOPHOSPHORUS COMPOUNDS FOR THE THERAPEUTIC AND PROPHYLACTIC TREATMENT OF INFECTIONS

(76) Inventor: Jomaa Hassan, Breslauer Str 24, 35398 Giessen (DE)

( * ) Notice: Subject to any disclaimer, the term of this patent is extended or adjusted under 35 U.S.C. 154(b) by 0 days.

(21) Appl. No.: 09/673,561
(22) PCT Filed: Apr. 13, 1999
(86) PCT No.: PCT/EP99/02462
§ 371 (c)(1),
(2), (4) Date: Dec. 8, 2000
(87) PCT Pub. No.: WO99/52515
PCT Pub. Date: Oct. 21, 1999

(30) Foreign Application Priority Data

| Apr. 14, 1998 | (DE) | 198 16 196 |
| Jun. 9, 1998 | (DE) | 198 25 585 |
| Sep. 22, 1998 | (DE) | 198 43 223 |
| Sep. 22, 1998 | (DE) | 198 43 222 |

(51) Int. Cl.[7] ............................................. A01N 57/00
(52) U.S. Cl. ....................................... 514/125; 514/75
(58) Field of Search ................................. 514/125, 75

(56) References Cited

U.S. PATENT DOCUMENTS

| 3,887,353 A | * | 6/1975 | Kerst et al. |
| 4,206,156 A | | 6/1980 | Kamiya et al. |
| 4,268,503 A | | 5/1981 | Imanaka et al. |
| 4,330,529 A | | 5/1982 | Imanaka et al. |
| 4,693,742 A | | 9/1987 | Patterson |
| 5,091,375 A | * | 2/1992 | Hector et al. |

FOREIGN PATENT DOCUMENTS

| DE | 27 33 658 | 2/1978 |
| EP | 0 009 686 | 4/1980 |
| EP | 0 256 785 | 2/1988 |
| JP | 51125750 | * 11/1976 |
| JP | 57 046917 | 3/1982 |
| WO | WO-96/32115 | * 10/1996 |
| WO | WO98/05294 | * 2/1998 |

OTHER PUBLICATIONS

Budavari, ed. The Merck Index, 11 th ed. 1989, monograph 3429.*
Charandabi et al., Phosphourus, Sulfur, and Silicon, 1989; 44:223–234.*
Katzung (Basic and Clinical Pharmacology, 1995, pp. 723–724, 730–733, 799–800.*
English Abstract of MIsato et al. JP51125750.*
H.C. Neu et al., "In Vitro and In Vivo Antibacterial Activity of FR–31564, a Phosphonic Acid Antimicrobial Agent," Antimicrob. Agents Chemother, vol. 19, No. 6, 1981, pp. 1013–1023.
H.C. Neu et al., "Synergy of Fosmidomycin and Other Antimicrobial Agents," Antimicrob. Agents Chemother., vol. 22, No. 4, 1982, pp. 560–563.
D. Greenwood, Fosfomycin Trometamol:Activity In Vitro Against Urinary Tract Pathogens, Infection, vol. 18, No. Suppl. 2, 1990, pp. S0–S64.
D. Greenwood, "Fosfomycin and fosmidomycin," Antibiot. Chemother. (7th Ed.), 1997, pp. 357–359.

* cited by examiner

Primary Examiner—Sreeni Padmanabhan
Assistant Examiner—San-ming Hui

(57) ABSTRACT

Use of organophosphorus compounds of general Formula (I)

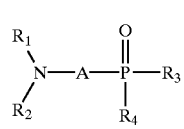

for the therapeutic and prophylactic treatment of infections in humans and animals caused by viruses, fungi and parasites.

16 Claims, 1 Drawing Sheet

USE OF ORGANOPHOSPHORUS COMPOUNDS FOR THE THERAPEUTIC AND PROPHYLACTIC TREATMENT OF INFECTIONS

This application is a 371 of PCT/EP99/02462, filed Apr. 13, 1999.

The invention relates to the use of organophosphorus compounds and their salts, esters and amides for the therapeutic and prophylactic treatment of infections which are caused by viruses, fungi and parasites in humans and animals. According to the invention the organophosphorus compounds comprise phosphonic acid derivatives, phosphinoyl derivates and phosphinic acid derivatives.

The suitability of aminohydrocarbyl phosphonic acid derivates and some of their esters and salts for use in pharmaceutical compositions is already known. Up until now however only their antimicrobial efficacy against bacteria in humans and animals and against fungi in plants has been described (DE 27 33 658 A1, U.S. Pat. No. 4,143,135, U.S. Pat. No. 4,182,758 and U.S. Pat. No. 4,206,156, U.S. Pat. No. 4,994,447, U.S. Pat. No. 4,888,330, U.S. Pat. No. 4,210,635, U.S. Pat. No. 3,955,958, U.S. Pat. No. 4,196,193, U.S. Pat. No. 4,268,503, U.S. Pat. No. 4,330,529, U.S. Pat. No. 5,189,030, U.S. Pat. No. 3,764,677, U.S. Pat. No. 3,764,676). Furthermore substances from this group have been described as herbicides (U.S. Pat. No. 4,693,742, U.S. Pat. No. 5,002,602, U.S. Pat. No. 4,131,448, U.S. Pat. No. 3,977,860, U.S. Pat. No. 4,062,669), as algaecides (U.S. Pat. No. 3,887,353), as means for regulating plant growth (U.S. Pat. No. 4,127,401, U.S. Pat. No. 4,120,688, U.S. Pat. No. 3,961,934, U.S. Pat. No. 4,431,438, U.S. Pat. No. 3,853,530, U.S. Pat. No. 4,205,977, U.S. Pat. No. 4,025,332, U.S. Pat. No. 3,894,861) and as reagents in dye production (U.S. Pat. No. 4,051,175). In DE 27 33 658 A1 the use of aminohydrocarbyl phosphonic acid derivatives for the treatment of bacterial diseases has been described. Whilst the document speaks of a microbial efficacy against pathogenic microorganisms in the introduction to the description, from the overall context however it is clear that the invention relates exclusively to bacteria. Thus on page 16, second paragraph "antimicrobial efficacy" is defined as "antibacterial efficacy".

There is a serious need for the provision of preparations to enhance the treatment of humans and animals and the protection of plants, which preparations not only possess a strong efficacy but in contrast to other pharmaceutical compositions and plant protective agents, contain reduced side effects and therefore represent a lower risk to health for humans.

The object of the present invention is therefore to provide a substance which fulfils the conditions given above in the case of infections caused by viruses, fungi and parasites in humans and animals.

This object is achieved in a completely surprising manner by the group of substances defined in claim 1. This group of substances demonstrates an anti-infectious effect against viruses, fungi and unicellular and multicellular parasites. In the context of this invention the strictly scientific definition of parasites is to be used. This means that unicellular parasites are understood to mean protozoa exclusively.

The organophosphorus compounds used according to the invention correspond to the general Formula (I):

in which $R_1$ and $R_2$ are the same or different and are selected from the group which consists of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, substituted and unsubstituted heterocyclic radical, halogen, $OX_1$ and $OX_2$, wherein $X_1$ and $X_2$ can be the same or different and are selected from the group which consists of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, substituted and unsubstituted heterocyclic radicals,

A is selected from the group which consists of an alkylene radical, an alkenylene radical and a hydroxyalkylene radical, $R_3$ and $R_4$ are selected independently from the group which consists of hydrogen, substituted and unsubstituted $C_{1-26}$-alkyl, substituted and unsubstituted hydroxy-$C_{1-26}$-alkyl, substituted and unsubstituted aryl, substituted and unsubstituted acyl, substituted and unsubstituted aralkyl, substituted and unsubstituted $C_{1-26}$-alkenyl, substituted and unsubstituted $C_{1-26}$-alkinyl, substituted and unsubstituted cycloalkyl, substituted and unsubstituted heterocyclic radical, halogen, $OX_3$ and $OX_4$, wherein $X_3$ and $X_4$ are selected independently from the group which consists of hydrogen, substituted and unsubstituted $C_{1-26}$-alkyl, substituted and unsubstituted hydroxyl-$C_{1-26}$-alkyl, substituted and unsubstituted aryl, substituted and unsubstituted aralkyl, substituted and unsubstituted $C_{1-26}$-alkenyl, substituted and unsubstituted $C_{1-26}$-alkinyl, substituted and unsubstituted cycloalkyl, substituted and unsubstituted heterocyclic radical, a silyl, a cation of an organic and inorganic base, in particular a metal of the first, second or third main group of the periodic system, ammonium, substituted ammonium and ammonium compounds which derive from ethylene diamine or amino acids, and their pharmaceutically acceptable salts, esters and amides and salts of esters. Phosphonic acid derivatives are particularly preferred.

In particular compounds which contain the following Formula (II) are suitable:

wherein, $X_1$ is selected from the group which consists of hydrogen, substituted or unsubstituted acyl, substituted or unsubstituted alkyl, substituted or unsubstituted aryl, substituted or unsubstituted aralkyl, substituted or unsubstituted cycloalkyl, substituted and unsubstituted heterocyclic radical;

$R_2$, $R_3$, $R_4$ and A contain the same meaning as in Formula (I)

A is particularly preferably a chain of three carbon atoms which bind the nitrogen atom to the phosphorus atom.

Compounds of Formula (II) are particularly preferred in which $R_2$=acyl, in particular an acetyl, $R_3$=hydrogen, methyl or ethyl, $R_4$=hydrogen, methyl, ethyl or $OX_4$ with $X_4$=hydrogen, sodium, potassium, methyl, ethyl, $X_1$=H and A=alkylene, alkenylene or hydroxyalkylene. Particularly good results are achieved with $R_2$=formyl or acetyl and A=propylene, propenylene or hydroxypropylene.

Furthermore compounds are particularly preferred in which $R_3$ is an alkyl, hydroxyalkyl, alkinyl, or alkenyl group with 16 or 18 carbon atoms or $OX_3$, wherein $X_3$ is an alkyl, alkinyl, hydroxyalkyl or alkenyl group with 16 or 18 carbon atoms, $R_4$ is an alkyl, alkinyl, hydroxyalkyl or alkenyl group with 16 or 18 carbon atoms or $OX_4$, wherein $X_4$ is an alkyl, alkinyl, hydroxyalkyl or alkenyl group with 16 or 18 carbon atoms.

Special features of the above definitions and suitable examples thereof are given below:

"Acyl" is a substituent which originates from an acid such as from an organic carboxylic acid, carbonic acid, carbamic acid or the thioacid or imidic acid corresponding to the individually present acids, or from an organic sulphonic acid, wherein these acids comprise in each case aliphatic, aromatic and/or heterocyclic groups in the molecule and carbamoyl or carbamimidoyl.

Suitable examples of these acyl groups will be given below.

Acyl radicals originating from an aliphatic acid are designated as aliphatic acyl groups and include:

Alkanoyl (for example formyl, acetyl, propionyl, butyryl, isobutyryl, valeryl, isovaleryl, pivaloyl etc.);

Alkenoyl (for example acryloyl, methacryloyl, crotonoyl etc.);

Alkylthioalkanoyl (for example methylthioacetyl, ethylthioacetyl etc.);

Alkane sulphfonyl (for example mesyl, ethane sulphonyl, propane sulphonyl etc.);

Alkoxycarbonyl (for example methoxycarbonyl, ethoxycarbonyl, propoxycarbonyl, isopropoxycarbonyl, butoxycarbonyl, isobutoxycarbonyl etc.);

Alkylcarbamoyl (for example methylcarbamoyl etc.);

(N-alkyl)-thiocarbamoyl (for example (N-methyl)-thiocarbamoyl etc.);

Alkylcarbamimidoyl (for example methylcarbamimidoyl etc.);

Oxalo;

Alkoxalyl (for example methoxalyl, ethoxalyl, propoxalyl etc.).

In the above examples of aliphatic acyl groups the aliphatic hydrocarbon part, in particular the alkyl group and the alkane radical can optionally contain one or more suitable substituents such as amino, halogen (for example fluorine, chlorine, bromine etc.), hydroxy, hydroxyimino, carboxy, alkoxy (for example methoxy, ethoxy, propoxy etc.), alkoxycarbonyl, acylamino (for example benzyloxycarbonylamino etc.), acyloxy (for example acetoxy, benzoyloxy etc.) and the like. Preferred aliphatic acyl radicals with such substitutes are for example alkanoyls substituted with amino, carboxy, amino and carboxy, halogen, acylamino or the like.

Acyl resides originate from an acid with substituted or unsubstituted aryl groups, wherein the aryl group can comprise phenyl, toluyl, xylyl, naphthyl, and the like are designated as aromatic acyl radicals. Suitable examples are given below:

Aroyl (for example benzoyl, toluoyl, xyloyl, naphthoyl, phthaloyl etc.);

Aralkanoyl (for example phenylacetyl etc.);

Aralkenoyl (for example cinnamoyl etc.);

Aryloxyalkanoyl (for example phenoxyacetyl etc.);

Arylthioalkanoyl (for example phenylthioacetyl etc.);

Arylaminoalkanoyl (for example N-phenylglycyl, etc.);

Arene sulphonyl (for example benzene sulphonyl, tosyl toluene sulphonyl, naphthalene sulphonyl etc.);

Aryloxycarbonyl (for example phenoxycarbonyl, naphthyl-oxycarbonyl etc.);

Aralkoxycarbonyl (for example benzyloxycarbonyl etc.);

Arylcarbamoyl (for example phenylcarbamoyl, naphthyl-carbamoyl etc.);

Arylglyoxyloyl (for example phenylglyoxyloyl etc.).

In the above-mentioned examples of aromatic acyl radicals the aromatic hydrocarbon part (in particular the aryl radical) and/or the aliphatic hydrocarbon part (in particular the alkane radical) can optionally contain one or more suitable substituents such as those which were already mentioned as suitable substituents for the alkyl group and the alkane radical. In particular and as an example of preferred aromatic acyl radicals with particular substituents, aroyl substituted by halogen and hydroxy or by halogen and acyloxy and aralkanoyl substituted by hydroxy, hydroxyimino, dihalogenalkanoyloxyimino are mentioned as well as Arylthiocarbamoyl (for example phenylthiocarbamoyl etc.);

Arylcarbamimidoyl (for example phenylcarbamimidoyl etc.).

A heterocyclic acyl radical is understood to be an acyl radical which originates from an acid with hererocyclic group. These include:

Heterocyclic carbonyl, in which the heterocyclic radical is an aromatic or aliphatic 5 to 6 membered heterocycle with at least one heteroatom from the group nitrogen, oxygen and sulphur (for example thiophenyl, furoyl, pyrrolcarbonyl, nicotinoyl etc.);

Heterocyclic alkanoyl in which the heterocyclic radical is 5 to 6 membered and has at least one heteroatom from the group nitrogen, oxygen and sulphur (for example thiophenylacetyl, furylacetyl, imidazolylpropionyl, tetrazolylacetyl, 2-(2-amino-4-thiazolyl)-2-methoxyiminoacetyl etc.) and the like.

In the above examples of heterocyclic acyl radicals the heterocycles and/or the aliphatic hydrocarbon part can optionally contain one or more suitable substituents, such as the same as those which were mentioned as suitable for alkyl and alkane groups.

"Alkyl" is a straight- or branched-chain alkyl radical with up to 9 carbon atoms, unless defined otherwise, such as methyl, ethyl, propyl, isopropyl, butyl, isobutyl, tertiary butyl, pentyl, hexyl and the like.

"Hydroxylalkyl" is a straight- or branched-chain alkyl radical with up to 9 carbon atoms, unless defined otherwise, which contains at least one hydroxyl group, preferably one or two hydroxyl groups.

"Alkenyl" includes straight- or branched-chain alkenyl groups with up to 9 carbon atoms, unless defined otherwise, such as, for example, vinyl, propenyl, (for example 1-propenyl, 2-propenyl), 1-methylpropenyl, 2-methylpropenyl, butenyl, 2-ethylpropenyl, pentenyl, hexenyl.

"Alkinyl" includes straight- or branched-chain alkinyl groups with up to 9 carbon atoms, unless defined otherwise.

Cycloalkyl preferably represents an optionally substituted C3 to C7 cycloalkyl. Alkyl, alkenyl, alkinyl, alkoxy (for example methoxy, ethoxy etc.), halogen (for example fluorine, chlorine, bromine etc.), nitro and the like are inter alia suitable as possible substituents.

Aryl is an aromatic hydrocarbon radical such as phenyl naphthyl etc., which can optionally contain one or more suitable substituents such as alkyl, alkenyl, alkinyl, alkoxy (for example methoxy, ethoxy etc.), halogen (for example fluorine, chlorine, bromine etc.), nitro and the like.

"Aralkyl" includes mono-, di-, triphenylalkyls such as benzyl, phenethyl, benzhydryl, trityl and the like, wherein the aromatic part can optionally contain one or more suitable substituents such as alkoxy (for example methoxy, ethoxy etc.), halogen (for example fluorine, chlorine, bromine etc.), nitro and the like.

"Alkylene" includes straight- or branched-chain alkylene groups which contain up to 9 carbon atoms and can be reproduced by the Formula in which n is an integer from 1 to 9, such as methylene, ethylene, trimethylene, methylethylene, tetramethylene, 1-methyltrimethylene, 2-ethylethylene, pentamethylene, 2-methyltetramethylene, isopropylethylene, hexamethylene, and the like. Preferred alkylene radicals contain up to 4 carbon atoms and radicals with 3 carbon atoms such as, for example, trimethylene are particularly preferred. The hydrogen atoms can be replaced by other substituents such as, for example, halogen radicals.

"Alkenylene" includes straight- or branched-chain alkenylene groups with up to 9 carbon atoms which can be reproduced by the Formula in which n is an integer from 2 to 9, such as, for example, vinylene, propenylene (for example 1-propenylene, 2-propenylene), 1-methylpropenylene, 2-methylpropenylene, butenylene, 2-ethylpropenylene, pentenylene, hexenylene and the like. The alkenylene radical can particularly preferably contain up to 5 carbon atoms and in particular 3 carbon atoms such as, for example, 1-propenylene. The hydrogen atoms can be replaced by other substituents such as, for example, halogen radicals.

"Hydroxyalkylene" can include straight- or branched-chain alkylene radicals which contain up to 9 carbon atoms, wherein at least one selected carbon atom is substituted by a hydroxy group. These radicals can be reproduced by the Formula in which n is an integer from 1 to 9 and z is an integer, to which $1 \leq z \leq n$ applies. Suitable examples of such hydroxyalkylene groups include hydroxymethylene, hydroxyethylene (for example 1-hydroxyethylene and 2-hydroxyethylene), hydroxytrimethylene (for example 1-hydroxytrimethylene, 2-hydroxytrimethylene and 3-hydroxytrimethylene), hydroxy-tetramethylene (for example 2-hydroxytetramethylene), 2-hydroxy-2-methyltrimethylene, hydroxypentamethylene (for example 2-hydroxypentamethylene), hydroxyhexamethylene (for example 2-hydroxyhexamethylene) and the like. A lower hydroxyalkylene with up to 4 carbon atoms is particularly preferred and in particular one with 3 carbon atoms such as, for example, 2-hydroxytrimethylene. The hydrogen atoms can be replaced by other substituents such as, for example, halogen radicals.

The radicals $X_3$ and $X_4$ can preferably be selected such that esters form on the phosphinic group or phosphonic group. Suitable examples of such esters in accordance with the Formulae (I) and (II) include alkyl esters (for example methyl ester, ethyl ester, propyl ester, isopropyl ester, butyl ester, isobutyl ester, hexyl ester, hexadecanyl ester, octadecanyl ester etc.);

Aralkyl esters (benzyl ester, phenethyl ester, benzohydryl ester, trityl ester etc.);

Aryl esters (for example phenyl ester, tolyl ester, naphthyl ester etc.);

Aroylalkyl esters (for example phenacyl ester etc.); and silyl esters (for example from trialkylhalogensilyl, dialkyldihalogensilyl, alkyltrihalogensilyl, dialkylarylhalogensilyl, trialkoxyhalogensilyl, dialkylaralkylhalogensilyl, dialkoxydihalogensilyl, trialkoxyhalogensilyl etc.) and the like.

With the above esters the alkane and/or arene part can contain at least one suitable substituent as desired such as halogen, alkoxy, hydroxy, nitro or the like.

$X_3$ and $X_4$ are preferably a metal from the first, second or third main group of the periodic system, ammonium, substituted ammonium or ammonium compounds which derive from ethylenediamine or amino acids. In other words the salt compounds of organophosphorus compounds are formed with organic or inorganic bases (for example sodium salt, potassium salt, calcium salt, aluminium salt, ammonium salt, magnesium salt, triethylamine salt, ethanolamine salt, dicyclohexylamine salt, ethylenediamine salt, N,N'-dibenzylethylenediamine salt etc.) and salts with amino acids (for example arginine salt, aspartic acid salt, glutamic acid salt etc.) and the like.

The compounds used according to the invention in accordance with the Formulae (I) or (II) can be present in their protonised form as ammonium salt of organic or inorganic acids such as hydrochloric acid, hydrobromic acid, sulphuric acid, nitric acid, methane sulphonic acid, p-toluene sulphonic acid, acetic acid, lactic acid, maleic acid, fumaric acid, oxalic acid, tartaric acid, benzoic acid etc.

The compounds used according to the invention of Formulas (I) or (II) permit for example the emergence of spatial isomers for groups containing double bonds or chiral groups $R_1$, $R_2$, $R_3$, $R_4$, $X_1$, $X_2$, $X_3$, $X_4$ or A. The use of compounds according to the invention consists of all spatial isomers both as pure substances and in the form of their mixtures.

The organophosphorus compounds are suitable in particular for the therapeutic and prophylactic treatment of infections in humans and animals which are caused by viruses, unicellular and multicellular parasites and fungi.

The compounds are effective against unicellular parasites (protozoa), in particular against pathogens of malaria and sleeping sickness as well as Chagas' disease, toxoplasmosis, amoebic dysentery, leishmaniasis, trichomoniasis, pneumocystosis, balantidiasis, cryptosporidiasis, sarcocystosis, acanthamebiasis, naegleriasis, coccidiosis, giardiasis and lambliosis.

They are therefore particularly suitable as malaria prophylactics and as prophylactics for sleeping sickness as well as Chagas' disease, toxoplasmosis, amoebic dysentery, leishmaniasis, trichomoniasis, pneumocystosis, balantidiasis, cryptosporidiasis, sarcocystosis, acanthamebiasis, naegleriasis, coccidiosis, giardiasis and lambliosis.

Combinations with an antibiotic can also be used to treat the above-mentioned diseases. Isoniazid, rifampicin, ethambutol, pyrazineamide, streptomycin, protionamide and dapsone are particularly suitable for combination with other anti-infectives for the treatment of tuberculosis.

The agents according to the invention can furthermore be used in particular in infections with the following viruses:

Parvoviridae: parvo viruses, dependo viruses, denso viruses,

Adenoviridae: adeno viruses, mastadeno viruses, aviadeno viruses,

Papovaviridae: papova viruses, in particular papilloma viruses (so called wart viruses), polyoma viruses, in particular JC virus, BK virus and miopapova viruses, Herpesviridae: all herpes viruses, in particular herpes simplex viruses, varicella-zoster viruses, human cytomegalo virus, Epstein-Barr viruses, all human herpes viruses, human herpes virus 6, human herpes virus 7, human herpes virus 8, Poxviridae: pox viruses, orthopox, parapox, molluscum contagiosum virus, avipox viruses, capripox viruses, leporipox viruses, all primary hepatotropic viruses, hepatitis viruses: hepatitis A viruses, hepatitis B viruses, hepatitis C viruses, hepatitis D viruses, hepatitis E viruses, hepatitis F viruses, hepatitis G viruses, Hepadna viruses: all hepatitis viruses, hepatitis B virus, hepatitis D viruses, Picornaviridae: picorna viruses, all entero viruses, all polio viruses, all coxsackie viruses, all echo viruses, all rhino viruses, hepatitis A virus, aphtho viruses, Calciviridae: hepatitis E viruses, Reoviridae: reo viruses, orbi viruses, rota viruses, Togaviridae: toga viruses, alpha viruses, rubi viruses, pestiviruses, rubella virus, Flaviviridae: flavi viruses, ESME virus, hepatitis C virus, Orthomyxoviridae: all influenza viruses, Paramyxoviridae: paramyxo viruses, morbilli virus, pneumo virus, measles virus, mumps virus Rhabdoviridae: rhabdo viruses, rabies virus, lyssa virus, viscula stomatitis virus, Coronaviridae: corona viruses, Bunyaviridae: bunya viruses, nairo virus, phlebo virus, uuku virus, hanta virus, hantaan virus, Arenaviridae: arena viruses, lymphocytic choriomeningitis virus, Retroviridae: retro viruses, all HTL viruses, human T-cell leukaemia virus, oncorna viruses, spuma viruses, lenti viruses, all HI viruses, Filoviridae: Marburg and Ebola virus, Slow virus infections, prions, Oncoviruses and leukaemia viruses.

The organophosphorus compounds used according to the invention are therefore suitable for fighting the following viral infections:

Eradication of papilloma viruses to prevent tumours, in particular tumours in the sexual organs caused by papilloma viruses in humans, eradication of JC viruses and BK viruses, eradication of herpes viruses, eradication of human herpes viruses 8 for the treatment of Kaposi's sarcoma, eradication of cytomegalo viruses before transplants, eradication of Epstein-Barr viruses before transplants and to prevent tumours associated with Epstein-Barr viruses, eradication of hepatitis viruses for the treatment of chronic liver diseases and for the prevention of tumours of the liver and cirrhosis of the liver, eradication of coxsackie viruses in patients with cardiomyopathy, eradication of coxsackie viruses in diabetes mellitus patients, eradication of immune system debilitating viruses in humans and animals, treatment of secondary infections in AIDS patients, treatment of inflammations of viral origin of the respiratory tract (larynx papillomas, hyperplasias, rhinitis, pharyngitis, bronchitis, pneumonias), of the sensory organs (keratoconjunctivitis), of the nervous system (poliomyelitis, meningoencephalitis, encephalitis, subacute sclerosing panencephalitis SSPE, progressive multifocal leukoencephalopathy, lymphocytic choriomeningitis), of the gastro-intestinal tract (stomatitis, gingivostomatitis, oesophagitis, gastritis, gastroenteritis, diarrhoea-causing diseases), of the liver and gall bladder system (hepatitis, cholangitis, hepatocellular carcinoma), of the lymphatic tissue (mononucleosis, lymphadenitis), of the haematopoetic system, of the sexual organs (mumpsorchitis), of the skin (warts, dermatitis, herpes labialis, heat rash, herpes zoster, shingles), of the mucous membranes (papillomas, conjunctiva papillomas, hyperplasias, dysplasias), of the heart/blood vessel system (arteritis, myocarditis, endocarditis, pericarditis), of the kidney/urinary tract system, of the sexual organs (anogenital lesions, warts, genital warts, acute condylomas, displasias, papillomas, cervix dysplasias, condylomata acuminata, epidermodysplasia verruci formis), of the organs of motion (myositis, myalgias), treatment of foot and mouth diseases in cloven-hoofed animals, of Colorado tick fever, of Dengue syndrome, of haemorrhagic fever, of early summer meningoencephalitis (ESME) and of yellow fever.

The described compounds, i.e. the organophosphorus compounds according to Formulae (I) and (II) and esters and amides thereof on the phosphinic group or phosphonic group and salts thereof have a strongly cytotoxic efficacy against unicellular and multicellular parasites, in particular against pathogens of malaria and sleeping sickness. Accordingly the compounds used according to the invention can be used for the treatment of infectious diseases which are caused by viruses, parasites and fungi in humans and animals. The compounds are also suitable for use in the prevention of diseases which are caused by viruses, parasites and fungi, in particular as malaria prophylactics and as sleeping sickness prophylactics.

The organophosphorus compounds used according to the invention, which generally include pharmaceutically acceptable salts, amides, esters, a salt of such an ester or else compounds which upon application provide the compounds used according to the invention as metabolic products or decomposition products, also called "prodrugs", can all prepared for administration like known anti-infectious agents in any suitable manner (mixed with a non-toxic pharmaceutically acceptable carrier). Pharmaceutically acceptable salts of the compounds include salts which form the compounds used according to the invention of Formulae (I) and (II) in their protonised form as an ammonium salt of inorganic or organic acids, such as hydrochloric acid, sulphuric acid, citric acid, maleic acid, fumaric acid, tartaric acid, p-toluene sulphonic acid.

Salts which are formed by suitable selection of $X_3$ and $X_4$ such as sodium salt, potassium salt, calcium salt, ammonium salt, ethanolamine salt, triethylamine salt, dicylcohexylamine salt and salts of an amino acid such as arginine salt, aspartic acid salt, glutamine acid salt are particularly suitable pharmaceutically.

The activity of substances is determined in a test system. This system is based on the measuring of the inhibition of growth of parasites, viruses, fungi or plants in vitro. To this end, test procedures are used, some of which are known to the person skilled in the art.

To determine the anti-malaria activity, for example, the inhibition of the growth of malaria parasites in blood cultures is determined.

The determining of antiviral activity is based on inhibition of the formation of viral elements in cell cultures.

The determining of fungicidal activity is based on the inhibition of the growth of fungi on culture media and in liquid cultures.

Some of the microorganisms which should be investigated can only be investigated in animal models. In this case we will use the corresponding models.

Substances which demonstrate an efficacy in the in vitro measuring systems will be further investigated in in vivo models.

The anti-parasitic, antiviral or fungicide activity will be further evaluated in the appropriate animal models.

The pharmaceutically effective preparations can be prepared in the form of pharmaceutical preparations in dispensing units. This means that the preparation can be present in the form of individual parts, for example tablets, dragees, capsules, pills, suppositories and ampoules, the active ingredient content of which corresponds to a fraction or a multiple of a single dose. The dispensing units can, for example, contain 1, 2, 3 or 4 single doses or ½, ⅓ or ¼ of a single dose. A single dose preferably contains the quantity of active ingredient which is administered during one application and which usually corresponds to a whole, a half or a third or a quarter of a daily dose.

Non-toxic, inert pharmaceutically suitable excipients are understood to mean solid, semi-solid or liquid diluents, fillers and formulation auxiliary agents of all kinds.

Tablets, dragees, capsules, pills, granules, suppositories, solutions, suspensions and emulsions, pastes, ointments, gels, creams, lotions, powders and sprays are mentioned as suitable pharmaceutical preparations. Tablets, dragees, capsules, pills and granules can contain in addition to the conventional excipients, the active ingredient or active ingredients such as (a) fillers and diluents, for example starches, lactose, cane sugar, glucose, mannitol and silicic acid, (b) binders, for example carboxymethylcellulose, alginates, gelatines, polyvinylpyrrolidone, (c) moisture-retaining agents, for example glycerol, (d) dispersing agents, for example agar-agar, calcium carbonate and sodium carbonate, (e) solution retarders, for example paraffin and (f) resorption accelerators, for example quaternary ammonium compounds, (g) wetting agents, for example cetyl alcohol, glycerol monostearate, (h) adsorption agents, for example kaolin and betonite and (i) lubricants, for example talcum, calcium and magnesium stearate and solid polyethylene glycols or mixtures of the substances listed under (a) to (i).

The tablets, dragees, capsules, pills and granular materials can be provided with the conventional coatings and casings optionally containing opaquing agents and can also be put together so that they release the active ingredient or active ingredients only or preferably in a specific part of the intestinal tract optionally with sustain release, wherein polymer substances and waxes for example can be used as embedding compounds.

The active ingredient or active ingredients can optionally also be present in microencapsulated form with one or more of the above-mentioned excipients.

In addition to the active ingredient or active ingredients suppositories can also contain the conventional water soluble or water insoluble excipients, for example polyethylene glycols, fats, for example cocoa fat and higher esters (for example C14-alcohol with C16-fatty acid) or mixtures of these substances.

In addition to the active ingredient or active ingredients, ointments, pastes, creams and gels can contain the conventional excipients, for example animal and vegetable fats, waxes, paraffins, starches, tragacanth, cellulose derivatives, polyethylene glycols, silicones, bentonites, silicic acid, talc and zinc oxide or mixtures of these substances.

In addition to the active ingredient or active ingredients, powders and sprays can contain the conventional excipients, for example lactose, talc, silicic acid, aluminium hydroxide, calcium silicate, and polyamide powder or mixtures of these substances. Sprays can additionally contain the conventional blowing agents, for example chlorofluorohydrocarbons.

In addition to the active ingredient or active ingredients, solutions and emulsions can contain the conventional excipients such as solvents, solubilisers and emulsifiers, for example water, ethyl alcohol, isopropyl alcohol, ethyl carbonate, ethyl acetate, benzyl alcohol, benzyl benzoate, propylene glycol, 1,3-butylene glycol, dimethyl formamide, oils, in particular cotton seed oil, peanut oil, corn oil, olive oil, castor oil and sesame oil, glycerol, glycerol formal, tetrahydrofurfuryl alcohol, polyethylene glycols and fatty acid esters of sorbitan or mixtures of these substances.

The solutions and emulsions can also be present in sterile and blood isotonic form for parenteral application.

In addition to the active ingredient or active ingredients, suspensions can contain conventional excipients such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances.

The above-mentioned formulations can also contain dyes, preservatives and odour and flavour improving additives, for example peppermint oil and eucalyptus oil and sweeteners, for example saccharine.

The agents of Formulae (I) and (II) should be present in the above-listed pharmaceutical preparations preferably in a concentration of approximately 0.1 to 99.5% by weight, preferably of approximately 0.5 to 95% by weight of the total mixture.

In addition to the compounds of Formulae (I) and (II) the pharmaceutical preparations can also contain further pharmaceutical agents.

The compounds can be used with hitherto described substances with antibacterial, antiviral, antifungal and anti-parasitic properties. Compounds which have already found application in treatment or are still being used belong to this group. Substances which are listed in the Red List or in Simon/Stille, Antibiotika-Therapie in Klinik und Praxis, 9th Edition 1998 Schattauer Verlag or under http:/www.customs.treas.gv/imp-exp/rulings/harmoniz/hrm129.html on the Internet are particularly suitable for this purpose. In particular derivatives with penicillins, benzyl penicillin (Penicillin G), phenoxy penicillins, isoxazolyl penicillins, amino penicillins, ampicillin, amoxicillin, bacampicillin, carboxy penicillin, ticarcillin, temocillin, acyalamino pencillins, azlocillin, mezlocillin, piperacillin, apalcillin, mecillinam, cephalosporins, cefazolin group, cefuroxime group, cefoxitin group, cefoxitin, cefotetan, cefmetazole, latamoxef, flomoxef, cefotaxime group, cefozidime, ceftazidime group, ceftazidime, cefpirom, cefepim, other cephalosporins, cefsulodine, cefoperazone, oralcephalosporins of the cefalexine group, loracarbef, cefprozil, new oral-cephalosporins with expanded spectrum, cefixime, cefpodoxim-proxetil, cefuroxime-axetil, cefetamet, cefotiam hexetil, cefdinir, ceftibutene, other β-lactam antibiotics, carbapenem, imipenem/cilastatin, meropenem, biapenem, aztreonam, β-lactamas inhibitors, calvulanic acid/amoxicillin, clavulanic acid/ticarcillin, sulbactam/ampicillin, tazobactam/piperacillin, tetracyclines, oxytetracycline, rolitetracycline, doxycycline, minocycline, chloramphenicol, aminoglycosides, gentimicin, tooramycin, netilmicin, amikacin, spectinomyxin, macrolides, erythromycin, clarithromycin, roxithromycin, azithromycin, di thromycin, spiramycin, josamycin, lincosamides, clindamycin, fusidic acid, glycopeptide antibiotics, vancomycin, tecoplanin, pristinamycin derivates, fosfomycin, antimicrobial folic acid antagonists, sulphonamides, co-trimoxazole, trimethoprim, other diaminopyrimidine-sulphonamide combinations, nitrofurans, nitrofurantoin, nitrofurazone, Gyrase inhibitors (quinolones), norfloxacin, ciprofloxacin, ofloxacin, sparfloxacin, enoxacin, fleroxacin, pefloxacin, lomefloxacin, Bay Y3118, nitroimidazoles, antimycobacterial agents, isoniazid, rifampicin, rifabutin, ethambutol, pyrazinamide, streptomycin, capreomycin, prothionamide, terizidon, dapsone, clofazimine, topical antibiotics, bacitracin, tyrothricin, polymyxins, neomycin, kanamycin, paromomycin, mupirocin, antiviral agents, acyclovir, ganciclovir, azidothymidine, didanosin, zalcitabin, thiacytidine, stavudine, ribavirin, idoxuridine, trifluridine, foscarnet, amantadine, interferons, tibol derivatives, proteinase inhibitors, antitungal agents, polyenes, amphotericin B, nystatin, natamycin, azoles, azoles for septic treatment, miconazole, ketoconazole, itraconazole, fluconazole, UK-109.496, azoles for topical application, clotrimazole, econazole, isoconazole, oxiconazole, bifonazole, flucytosine, griseofulvin, ciclopiroxolamine, tolnaftate, naftifine, terbinafine, amorolfine, anthraquinones, betulinic acid, semianthraquinones, xanthones, napthtoquinones, aryaminoalcohols, quinine, quinidines, mefloquine, halofantrine, chloroquine, amodiaquine, acridine, benzonaphthyridine, mepacrine, pyronaridine, dapsone, sulphonamide, sulfadoxine, sulfalenes, trimethoprim, proguanil, chlorproguanil, diaminopyrimidine, pyrimethamine, primaquine, aminoquinolines, WR 238,605, tetracycline, doxycyline, clindamycin, norfloxacin, ciprofloxacin, ofloxacin, artemisinin, dihydroartemisinin, lob arte mether, arte ether, arte sunate, atovaquon, suramin, melarsoprol, nifurtimnox, stibogluconate-sodium, pentamidine, amphotericin B, metronidazole, clioquinol, mebendazole, niclosamide, praziquantel, pyrantel, tiabendazole, diethylcarbamazine, ivermectin, bithionol, oxamniquine, metrifonate, piperazine, embonate can be [used].

The organophosphorus compounds can furthermore be present in the pharmaceutical preparations in combination with sulphonamide, sulfadoxin, artemisinine, atovaquon, quinine, chloroquine, hydroxychloroquine, mefloquine, halofantrine, pyrimethamine, armesin, tetracyclines, doxycycline, proguanil, metronidazole, praziquantel, niclosamide, mebendazole, pyrantel, tiabendazole, diethylecarbamazine, piperazine, pyrivinum, metrifonate, oxamniquine, bithionol or suramin or several of these substances.

The above-listed pharmaceutical preparations are produced in the conventional manner by known methods, for example by mixing the active ingredient or active ingredients with the excipient or excipients.

The above-mentioned preparations can be used in humans and animals either orally, rectally, parenterally, (intravenously, intramuscularly, subcutaneously), intracisternally, intravaginally, intraperitoneally, topically (powder, ointment, drops) and for the treatment of infections in cavities, orifices. Suitable preparations are injection solutions, solutions and suspensions for oral treatment, gels, infusions, emulsions, ointments or drops. Ophthalmological and dermatological formulations, silver and other salts, eardrops, eye ointments, powders or solutions can be used for topical treatment. With animals the absorption can occur via the food or drinking water in suitable formulations. Furthermore gels, powders, tablets, sustain release tablets, premixes, concentrates, granules, pellets, tablets, boli, capsules, aerosols, sprays, inhalers can be used with humans and animals. The compounds used according to the invention can furthermore be incorporated into other carrier materials such as, for example, plastics materials (plastics chains for topical treatment), collagen or bone cement.

In general it has proved advantageous both in human and veterinary medicine to administer the active ingredient or active ingredients of Formulae (I) and (II) in total quantities of approximately 0.05 to approximately 600, preferably 0.5 to 200 mg/kg body weight every 24 hours, optionally in the form of several individual doses in order to achieve the desired results. An individual dose contains the active ingredient or active ingredients preferably in quantities from approximately 1 to approximately 200, in particular 1 to 60 mg/kg body weight. It may however be necessary to deviate from the above-mentioned dosages and this is dependent on the nature and the body weight of the patient to be treated, the nature and the severity of the disease, the nature of the preparation and the application of the pharmaceutical composition as well as the time scale or interval within which the administration takes place.

Thus in some cases it may be sufficient to get by with less than the above-mentioned quantity of active ingredient whilst in other cases the above-stated quantity of active ingredient must be exceeded. The person skilled in the art can determine the optimum dosage and method of application of the active ingredient required in each case by virtue of their expert knowledge.

The compounds according to the invention can be given in the conventional concentrations and preparations to animals together with the feedstuff or the feedstuff preparations or with the drinking water.

EXAMPLE 1

Test of the Efficacy of Substances Against Malaria in Vivo

The various derivatives were tested by the modified Peters' test. The substances were applied here in a quarter of the median lethal dose (LD50). In the test batch ten mice were infected with *Plasmodium vinckeii*, the pathogen of mouse malaria. After confirmation of the infection by blood testing four mice were treated. Six mice, which were not treated, served as a control group. The treatment with 1,000 mg/kg/d, 3-(N-formyl-N-hydroxylamino)-propylphosphonic acid monosodium salt over 3 days led to a destruction of the parasites in the mice's blood. After just one day the treated group was free of living parasites. The control mice had to be killed on day 5 after infection with parasitaemia of >80%. The treated mice were still free from parasites 8 weeks after the treatment had stopped. Further experiments showed an efficacy of 50 mg/kg/d 3-(N-formyl-N-hydroxylamino)-propylphosphonic acid monosodium salt in mice with a parasitaemia of 80%. These mice were also free of living parasites after 1 day.

EXAMPLE 2

Protection from Malaria in a Test with Infected Mice

The efficacy of compounds in vivo against malaria was tested using male mice weighing 20 to 25 g (BALB/c-strain). Four mice were treated intraperitoneally with 50 mg/kg 3-(N-formyl-N-hydroxylamino)-propylphosphonic acid monosodium salt one day before infection. The mice were then infected with *Plasmodium vinckeii*. Mice which were not pretreated with the substance served as a control group. No infection could be detected in the treated mice, whilst the control mice were killed after 5 days with a parasitaemia of 80%. The treated mice were still free of parasites 8 weeks after infection.

EXAMPLE 3

In Vitro Cytotoxicity Against Malaria Parasites
On the Principle of IC50 Determination According to Vial et al (the Concentration at Which the Vitality of Parasites is Reduced by a Half)

Figure 1:
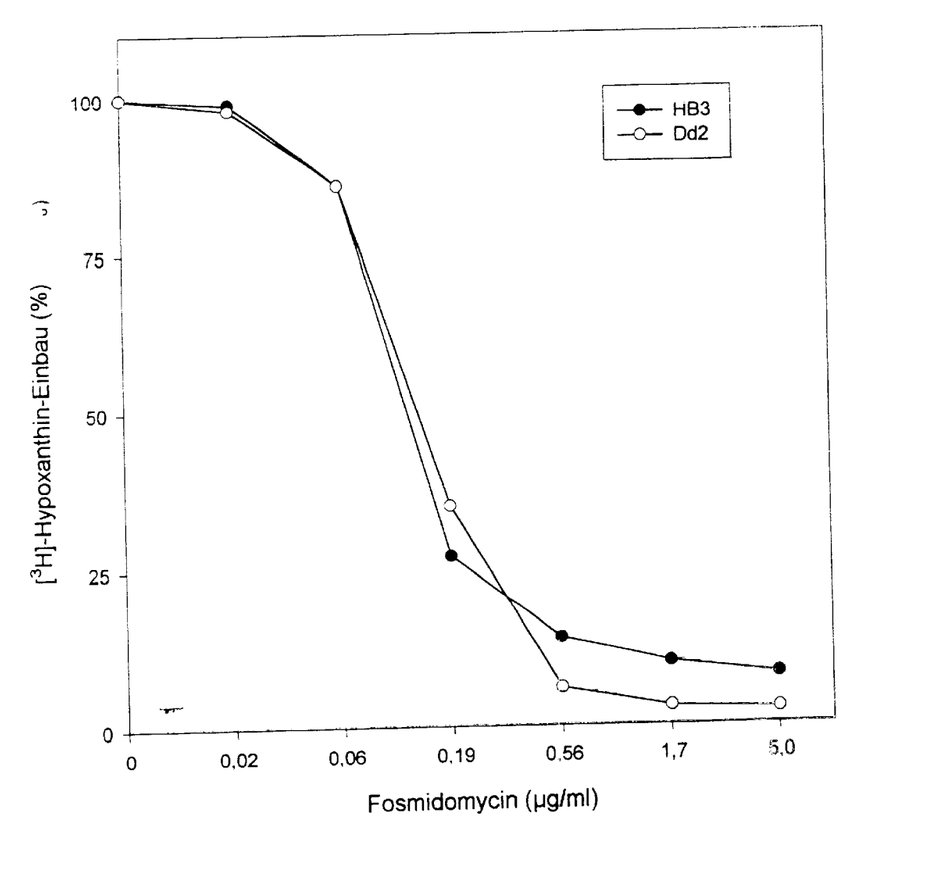

To determine the IC50 value according to Vial et al malaria parasites are initially cultivated for a complete 48 hour cycle in the presence of inhibitors, in the subsequent 24 hours the survival rate is measured by [$^3$H]-hypoxanthine insertion.
Carrying Out the Test A dilution series of 3-(N-formyl-N-hydroxylamino)-propylphosphonic acid monosodium salt is placed in 20 µl aliquots concentrated by 10 on a microtitre plate. Then 180 µl parasite suspension in culture medium is added to each well. Asynchronous cultures with a parasitaemia of approximately 0.4% and 2% haematocrite are used. The microtitre plates are subsequently incubated for 48 hours. Then 30 µl [$^3$H]-hypoxanthine are added to each well. After 24 hours of incubation the cells were harvested and the incorporated radioactivity was measured. In FIG. 1 the results with the strains HB3 and Dd2 are shown with known resistances against other malaria pharmaceutical compositions. In both strains there is a IC50 value of approximately 100 µg/l. The resistances of these strains are:

*Plasmodium falciparum* HB3 (Honduras) is resistant to pyrimethamine.

*Plasmodium falciparum* Dd2 (Indo-China) is resistant to cloroquine, quinine, pyrimethamine, cycloguanil and sulfadoxine.

No cross resistances with antimalarial agents were found.

EXAMPLE 4

Preparation of 3-Bromopropylphosphonic Acid Diethylester 471 g (238 ml, 2.33 mol) 1,3-dibromopropane and 77.6 g (81 ml, 0.467 mol) triethylphosphite were introduced into a 500 ml flask and heated for 30 minutes to 155–160° C. 20 ml ethyl bromide (boiling point: 40° C.) were distilled off under normal pressure via a reflux condenser and a distilling apparatus. Concentration of the solution under vacuum (8 torr (1.07·10$^3$ Pa)) resulted in 380 g (191 ml, 1.863 mol) 1.3 dibromopropane (surplus educt). 88.1 g (0.34 mol) could be distilled as a colourless liquid (boiling point: 96° C., 0.1 torr (13.33 Pa)) from the remaining yellow oil. This corresponds to a yield of 73%. (Hewitt, Teese, Aust.J.Chem. 1984, 37, 205–10 U.S. Pat. No. 4,206,156).

$^1$H-NMR (CDCl$_3$) δ=4.08 (quintet, J=7 Hz, 4H), 1.33 (t, J=7 Hz, 6H); $^{13}$C-NMR (CDCl$_3$) δ=61.2 (OCH$_2$CH$_3$), 33.10 (J=18, 3 Hz), 25.6 (J=4, 4 Hz), 24.14 (J=120, 6 Hz) 16.04 (OCH$_2$CH$_3$).

EXAMPLE 5

Preparation of 3-(N-Hydroxyamino)-propylphosphonic Acid Diethylester

Firstly 32.0 g (0.8 mol) of sodium hydroxide dissolved in 75 ml water then 75 ml methanol, and finally 25.5 g (0.098 mol) 3-bromopropyl phosphonic acid diethylester were added drop by drop to a solution of 55.6 g (0.8 mol) hydroxylamine hydrochloride in 100 ml water with cooling with ice. This led to a clouding of the solution. After 3 hours stirring at a temperature of 40 to 45° C. methanol was removed under reduced pressure, the resulting aqueous solution was saturated with NaHCO$_3$ (pH=8), shaken out three times with 60 ml toluene in each case (the toluene phase was discarded) and then shaken out with chloroform (1× with 90 ml, 2× with 50 ml in each case). The slightly yellowy chloroform phase was dried over MgSO$_4$. After filtering of the dehydrating agent the solution was concentrated under reduced pressure. 15.43 g (0.0728 mol) 3-(N-hydroxyamino)-propylphosphonic acid diethylester were obtained as an almost colourless oil. This corresponds to a yield of 74.3% (DE-A-27 33 658).

$^1$H-NMR (CDCl$_3$) δ=5.94 (wide s, 2H), 4.13 (quintet, J=7 Hz, 4H) 2.90 (t, J=7 Hz, 2H) 1.5–2.2 (m, 4H), 1.33 (t, J=7 Hz, 6H); $^{13}$C-NMR (CDCl$_3$) δ=61.23 (OCH$_2$CH$_3$), 53.34 (NCH$_2$, J=15, 9 Hz), 22.75 (J=141, 9 Hz), 19.77 Hz, 16.08 (OCH$_2$CH$_3$).

EXAMPLE 6

Preparation of 3-(N-Hydroxyamino)-propylphosphonic Acid 12.9 g (0.0608 mol) 3-(N-hydroxylamino)-propylphosphonic acid diethylester and 130 ml concentrated HCl were heated for 6 hours under reflux (oil bath temperature: 150° C.). The resulting yellow/orange solution is concentrated under-reduced pressure. The remaining oil is taken up in 30 ml water, stirred with 3 spoonfuls of activated carbon for 30 minutes, filtered out from the activated carbon and the colourless solution is concentrated in the entire diaphragm pump vacuum. After take-up in 30 ml water a pH of 4.0 to 4.5 is adjusted with approximately 4.7 g (0.056 mol) NaHCO$_3$ (from pH=1.5 the product precipitates). Suction filtering of the white solid resulted in 5.83 g 3-(hydroxyamino)-propylphosphonic acid (melting point: 160° C., decomposition). This corresponds to a yield of 61.8%. (DE-A-27 33 658, Öhler Synthesis 1995, 539–543).

$^1$H-NMR (CDCl$_3$) δ=3.49 (t, J=7, 4 Hz, 2H), 2.1 (m, 2H), 1.82 (m, PCH$_2$, 2H); $^{13}$C-NMR (CDCl$_3$) δ=56.26 (NCH$_2$, J=15 Hz), 29.61 (PC, J=134 Hz), 22.37 (C-2, J=3, 8 Hz).

EXAMPLE 7

Preparation of 3-(N-Formylhydroxyamino)-propylphosphonic Acid Diethylester 1.38 (0.030 mol) formic acid were added drop by drop at room temperature to 2.04 g (0.020 mol) acetic anhydride and stirred at the same temperature. This solution was added with cooling with ice to 2.8 g (0.013 mol) 3-(N-hydroxyamino)-propylphosphonic acid diethylester dissolved in chloroform. The reaction mixture is stirred for 30 minutes at 0–5° C. and for a further 1.5 hours at room temperature. After concentration under reduced pressure until an oily residue is obtained, this oily residue is taken up in 15 ml methanol and 5 ml water, adjusted to pH=8 with 2 n NaOH and stirred for a further 1.5 hours at room temperature. Methanol is removed under reduced pressure and the resultant aqueous solution is adjusted to pH=5 with concentrated HCl. The yellow solution is extracted with chloroform (1×30 ml, 2×10 ml in each case) and the $CHCl_3$ phases are dried over $MgSO_4$. After concentration of the solution in the entire diaphragm pump vacuum 3 g of a yellow oil are obtained. After removal of volatile constituents in the entire diaphragm pump vacuum, chromatography on 60 g $SiO_2$ with chloroform shows: methanol in the ratio 25:1 2.65 g product as yellow oil (DE-A-27 33 658).

$^1$H-NMR (CDCl$_3$) $\delta$=8.4 (CHO, 0.5 H), 7.94 (CHO, 0.5 H), 4.1 (quintet, 4 H), 3.68 (t, 2 H), 1.7–2.19 (m, 4 H), 1.36 (t, J=7 Hz, 6 H); $^{13}$C-NMR (CDCl$_3$) $\delta$=162.65 (CHO), 156.96 (CHO), 61.72 (O$\underline{C}H_2CH_3$), 46.31 (NCH$_2$, J=15, 9 Hz), 22.15 (PC, J=142, 0 Hz), 19.13 (C-2), 16.08 (OCH$_2$ $\underline{C}H_3$)

EXAMPLE 8

Preparation of 3-(N-Acetylhydroxyamino)-propylphosphonic Acid Diethylester 2.8 g (0.013 mol) 3-(N-hydroxyamino)-propylphosphonic acid diethylester are dissolved in 30 ml methylene chloride and added drop by drop with cooling with ice to 2.65 g (0.026 mol) acetic anhydride. The reaction mixture is stirred for 30 minutes at 0–5° C. and for a further 1.5 hours at room temperature. After concentration under reduced pressure until a yellow oily radical is achieved, this oily residue is taken up in 15 ml methanol and 5 ml water, adjusted to pH 8 with 2 n NaOH and stirred for a further 1.5 hours at room temperature. Methanol is removed under reduced pressure and the resultant solution is adjusted to pH=5 with concentrated HCl. The yellow solution is extracted repeatedly with methylene chloride (1×30 ml, 2×10 ml in each case), the combined $CH_2Cl_2$ phases are dried over $MGSO_4$ and the solvent is removed at room temperature under reduced pressure. 3.7 g of a yellow oil are obtained which are freed from adhering volatile substances in the entire diaphragm pump vacuum. 2.78 g yellow oil remain.

$^{13}$C-NMR (CDCL$_3$) $\delta$=171.96 (C=O), 61.62 (O $\underline{C}H_2CH_3$), 47.44 (J=15, 49 Hz), 22.13 (PC, J=141, 8 Hz), 19.3, 15.9 (OCH$_2$$\underline{C}H_3$)

EXAMPLE 9

Preparation of 3-(N-Formylhydroxyamino)-propylphosphonic Acid Monosodium Salt 2 ml formic acid are added drop by drop to 4 ml acetamide at 0–5° C. The solution is stirred at this temperature for 10 minutes and for a further 15 minutes at room temperature, subsequently cooled to 0° C. again and 3.28 g (0.021 mol) 3-(N-hydroxyamino)-propylphosphonic acid dissolved in 6 ml formic acid are added drop by drop at 0–5° C. After 1 hour of stirring at room temperature the solution is condensed in a rotary evaporator under reduced pressure, the oil is dissolved in 50 ml methanol, heated to 60° C. and mixed with 10 ml ethanol. The resulting oily separated material is separated without stirring by decanting. To precipitate white crystals the methanolic solution is mixed with a further 50 ml ethanol, boiled up and the white residue filtered out. This residue is taken up in 80 ml methanol and 100 ml ethanol are added with stirring. The mixture is stirred further overnight at room temperature. A solid is obtained which is filtered out. (DE-A-27 33 658)

EXAMPLE 10

Preparation of 3-(N-Acetylhydroxyamino)-propylphosphonic Acid Monosodium Salt

A suspension of 3.8 g (0.02 mol) 3-(N-hydroxyamino)-propylphosphonic acid is introduced into 20 ml water and 4.51 g (0.044 mol) acetic anhydride are added drop by drop at room temperature. After the solution has been stirred for 1.5 hours at room temperature a pH of 2.5 is adjusted with 0.2 n NaOH, the solution is concentrated in the entire diaphragm pump vacuum, taken up twice in 40 ml water in each case, which are again removed by concentration and the oil is washed twice with 30 ml ether in each case, taken up in 50 ml water and a pH of 6.5 is adjusted with 1.6 g NaHCO$_3$. After removal of volatile constituents under vacuum, 20 ml n-butanol are added to remove the residual water and are also removed under reduced pressure. The oil is boiled up twice with isopropanol, the isopropanol phase is discarded and the remaining glassy resin is pulverised with a spatula to a yellow solid (5.65 g). In order to recrystallise it, it is taken up in only a little methanol, filtered from the undissolved component and acetone is added dropwise to the filtrate. A first filtering results in 1 g product with a melting point of 175° C. Recrystallisation as described above is carried out again for further purification. (DE-A-27 33 658)

EXAMPLE 11

Preparation of Antiparasitically Effective Agents

Preparation for Injections:

(1) The required quantity of sterile antiparasitically effective agent, 3-(N-formyl-N-hydroxylamino)-propylphosphonic acid monosodium salt was divided into phials or ampoules which then contained 500 mg active ingredient. The phials were hermetically sealed to exclude bacteria. For injections 2 ml sterile water were added to the phials in each case and the content was administered.

In substantially the same manner as described under (1) further injectable preparations of the antiparasitically effective agent were prepared as described below:

(2) 250 mg 3-(N-formyl-N-hydroxylamino)-propylphosphonic acid monosodium salt were used as active ingredient for the injections.

(3) 250 mg 3-(N-formyl-N-hydroxylamino)-trans-1-propenyl-phosphonic acid monosodium salt were used as active ingredient for the injections.

(4) 500 mg 3-(N-acetyl-N-hydroxylamino)-2-hydroxypropyl-phosphonic acid monosodium salt were used as active ingredient for the injections.

(5) 250 mg 3-(N-formyl-N-hydroxylamino)-2-hydroxypropyl-phosphonic acid monopotassium salt were used as active ingredient for the injections.

Preparation of tablets:
A suitable tablet recipe is formed by the following mixture:

| | |
|---|---|
| 3-(N-formyl-N-hydroxylamino)-propylphosphonic acid monosodium salt | 200 mg |
| Mannitol | 400 mg |
| Starch | 50 mg |
| Magnesium stearate | 10 mg |

Preparation of Capsules:

| | |
|---|---|
| 3-(N-formyl-N-hydroxylamino)-propylphosphonic acid monopotassium salt | 300 mg |
| Magnesium stearate | 15 mg |

The present components were mixed and then introduced into a hard gelatine capsule in the conventional manner.

Preparation of an oily suspension:

| | |
|---|---|
| 3-(N-acetyl-N-hydroxylamino)-propylphosphonic acid monosodium salt | 200 mg |
| Lanette-Wax SX ® | 50 mg |
| Soft paraffin | 100 mg |
| Brilliant blue FCF | 25 mg |

The above components were mixed with liquid paraffin for a total quantity of 3 g to achieve an infusion preparation.

Examples of Methods of Synthesis for Substances With the Following Structure where $R_1 = R_2 = C_{18}H_{37}$    12
where $R_1$ = H or $Na^+$ and $R_2 = C_{18}H_{37}$    13
where $R_1$ = H or $Na^+$ and $R_2 = C_{16}H_{33}$    14

EXAMPLE 12

3-(N-Formyl-N-hydroxylamino)-propylphosphonic Acid Dioctadecyl-ester 12

1 equivalent fosmidomycin (FR-31564) and 6 equivalents tris(octadecyl)-orthoformic acid were heated under reduced pressure and vigorous stirring for 2 hours under reflux. Then methanol and formic acid octadecylester were distilled off—also under reduced pressure—wherein the temperature must be kept below the decomposition temperature of the product. Further volatile secondary products are removed in the oil pump vacuum in order finally to obtain 12 as a highly viscous oil. (On the carrying out of the procedure cf.: D. A. Nicholson, W. A. Cilley, O. T. Quimby, J Org Chem. 1970, 35, 3149–50)

The monoesters can be provided starting from both fosmidomycin and di-octadecylester 12.

EXAMPLE 13

3-(N-Formyl-N-hydroxylamino)-propylphosphonic Acid Monooctadecyl-ester 13

First Proposal:

0.21 mmol fosmidomycin (phosphonic acid) and 0.2 mmol n-octadecanol are dissolved in 1–2 ml dry pyridine and 0.67 mmol trichloracetonitrile is added dropwise thereto. The reaction mixture is heated for 16 hours to 80° C. and then condensed under vacuum. After take up in water (for the diaphragm filtering of undissolved components) the solution is condensed again under reduced pressure and the product is chromatographed onto silica gel with ethyl acetate, ethanol and water as eluent. The product 13 is produced in this case as a viscous rubber-like to glass-like compound. (On the carrying out of the procedure cf.: G. B. Brookes, D. Edwards, J. D. I. Hatto, T. C. Smale, R. Southgate, Tetrahedron 1995, 51, 7999–814)

Second Proposal:

0.2 mmol of the diester 3-(N-formyl-N-hydroxylamino)-propylphosphonic acid dioctadecylester 13 dissolved in ethanol is added to 1 equivalent KOH (ethanolic solution) and boiled for 10 hours under reflux. Owing to the introduction of $CO_2$, potassium salts can precipitate as carbonates and can be removed by filtration. The filtrate is condensed to dryness, the oil is dried over $P_2O_5$, washed with petrol ether and the product can finally be recrystallised from absolute ethanol by the addition of isopropanol.

(On the carrying out of the procedure cf.: V. Jagodic, Chem Ber 1960, 93, 2308–13)

EXAMPLE 14

3-(N-Formyl-N-hydroxylamino)-propylphosphonic Acid Monohexadecyl-ester 14

14 can be synthesised in the same way as 13.

What is claimed is:

1. A method for treating infections caused by parasites, fungi, and viruses in an individual, comprising:
   administering to the individual a pharmaceutical composition, comprising:
   (i) an organophosphorous compound or its pharmaceutically acceptable salt, wherein the organophosphorous compound is selected from the group consisting of 3-(N-formyl-N-hydroxylamino)-propylphosphonic acid, 3-(N-formyl-N-hydroxylamino)-trans-1-propenyl-phosphonic acid, 3-(N-acetyl-N-hydroxylamino)-2-hydroxypropyl-phosphonic acid, and 3-(N-formyl-N-hydroxylamino)-2-hydoxypropyl-phosphonic acid; and
   (ii) an excipient.

2. A method of treating an infection caused by a fungus in an individual, comprising:
   administering to the individual a composition comprising a pharmaceutically acceptable excipient and an effective amount of an organophosphorous compound of the general formula (1):

(I)

wherein:
   $R_1$ and $R_2$ are independently selected from the group consisting of substituted and unsubstituted hydroxyalkyl, substituted and unsubstituted alkenyl, substituted and unsubstituted alkinyl, substituted and unsubstituted aryl, unsubstituted acyl, substituted and unsubstituted cycloalkyl, substituted and unsubstituted aralkyl, substituted and unsubstituted heterocyclic radical, halogen, OX₁, and OX₂, wherein X₁ and X₂ are independently selected from the group consisting of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted aralkyl, and substituted and unsubstituted heterocyclic radical;

A is a 2–9 carbon moiety selected from the group consisting of alkylene radical, alkenylene radical, and hydroxyalkylene radical, wherein A includes a straight chain of at least two carbon atoms between the nitrogen atom and the phosphorus atom of general formula (I);

R₃ and R₄ are independently selected from the group consisting of hydrogen, substituted and unsubstituted C₁₋₂₆-alkyl, substituted and unsubstituted hydroxy-C₁₋₂₆-alkyl, substituted and unsubstituted aryl, substituted and unsubstituted acyl, substituted and unsubstituted aralkyl, substituted and unsubstituted C₁₋₂₆-alkenyl, substituted and unsubstituted C₁₋₂₆-alkinyl, substituted and unsubstituted cycloalkyl, substituted and unsubstituted heterocyclic radical, halogen, OX₃, and OX₄, wherein X₃ and X₄ are independently selected from the group consisting of hydrogen, substituted and unsubstituted C₁₋₂₆-alkyl, substituted and unsubstituted hydroxyl-C₁₋₂₆-alkyl, substituted and unsubstituted aryl, substituted and unsubstituted aralkyl, substituted and unsubstituted C₁₋₂₆-alkenyl, substituted and unsubstituted C₁₋₂₆-alkinyl, substituted and unsubstituted cycloalkyl, substituted and unsubstituted heterocyclic radical, silyl, a metal of the first, second or third main group of the periodic table, ammonium, substituted ammonium, ammonium salt of ethylene diamine, and ammonium salt of an amino acid, or an organic or inorganic acid salt thereof.

3. The method of claim 2 wherein the organophosphorous compound is of the Formula (II):

(II)

wherein:

X₁ is selected from the group consisting of hydrogen, substituted or unsubstituted acyl, substituted or unsubstituted alkyl, substituted or unsubstituted aryl, substituted or unsubstituted aralkyl, substituted or unsubstituted cycloalkyl, and substituted or unsubstituted heterocyclic radical.

4. The method of claim 2 wherein R₂ is selected from the group consisting of formyl radical and acetyl radical.

5. The method of claim 2 wherein R₃ and R₄ are independently selected from the group consisting of hydrogen, methyl, ethyl, OX₃ and OX₄, wherein X₃ and X₄ are independently selected from the group consisting of hydrogen, sodium, potassium, methyl and ethyl.

6. The method of claim 2 wherein R₄ is OX₄, wherein X₄ is selected from the group consisting of hydrogen, sodium, potassium, methyl, ethyl, ammonium, calcium, magnesium, ethanolamine, ethylenediamine, N,N-dibenzylethylenediamine, and arginine.

7. The method of claim 2 wherein A is selected from the group consisting of propylene, propenylene, and hydroxypropylene.

8. The method of claim 2 wherein the composition further comprises a component selected from the group consisting of sulphonamide, sulfadoxine, artemisinin, atovaquon, quinine, chloroquine, hydroxychloroquine, mefloquine, halofantrine, pyrimethamine, tetracyclines, doxycycline, proguanil, metronidazole, praziquantel, niclosamide, mebendazol, pyrantel, tiabendazol, diethylcarbazine, piperazine, pyrivinum, metrifonate, oxamniquine, bithionol, and suramin.

9. The method of claim 2 wherein the composition further comprises a component selected from the group consisting of benzyl penicillin, phenoxy penicillins, isoxazolyl penicillins, amino penicillins, ampicillin, amoxicillin, bacampicillin, carboxy penicillin, ticarcillin, temocillin, acyalamino pencillins, azlocillin, mezlocillin, piperacillin, apalcillin, mecillinam, cephalosporins, cefazolin, cefuroxime, cefoxitin, cefotetan, cefinetazole, latamoxef, flomoxef, cefotaxime, cefozidime, ceftazidime, cefpirom, cefepim, cefsulodine, cefoperazone, laracarbef, cefprozil, cefixime, cefpodoxim proxetil, cefuroxime axetil, cefetamet, cefotiam hexetil, cefdinir, ceftibutene, β-lactam antibiotics, carbapenem, imipenem/cilastatin, meropenem, biapenem, aztreonam, β-lactamase inhibitors, calvulanic acid/amoxicillin, calvulanic acid/ticarcillin, sulbactam/ampicillin, tazobactam/piperacillin, tetracyclines, oxytetracycline, roli-tetracycline, doxycycline, minocycline, chloramphenicol, amino-glycosides, gentamicin, tobramycin, netilmicin, amikacin, spectinomyxin, macrolides, erythromycin, clarithromycin, roxithromycin, azithromycin, dirithromycin, spiramycin, josamycin, lincosamides, clindamycin, fusidic acid, vancomycin, tecoplanin, pristinamycin, fosfomycin, antimicrobial folic acid antagonists, sulphonamides, co-trimoxazole, trimethoprim, diaminopyrimidine-sulphonamide combinations, nitrofurans, nitrofurantoin, nitrofurazone, Gyrase inhibitors, norflaxacin, ciproflaxacin, ofloxacin, sparfloxacin, enoxacin, fleroxacin, pefloxacin, lomefloxacin, nitroimidazoles, antimycobacterial agents, isoniazid, rifampicin, rifabutin, ethambutol, pyrazinamide, streptomycin, capreomycin, prothionamide, terizidon, dapsone, clofazimine, topical antibiotics, bacitracin, tyrothricin, polymyxins, neomycin, kanamycin, paromomycin, mupirocin, antiviral agents, acyclovir, ganciclovir, azidothymidine, didanosin, zalcitabin, thiacytidine, stavudine, ribavirin, idoxuridine, trifluridine, foscarnet, amantadine, interferons, antifungal agents, amphotericin B, nystatin, natamycin, miconazole, ketoconazole, itraconazole, fluconazole, clotrimazole, econazole, isoconazole, oxiconazole, bifonazole, flucytosine, griseofulvin, ciclopiroxolamine, tolnaftate, naftifine, terbinafine, amorolfine, anthraquinones, betulinic acid, semianthraquinones, xanthones, quinine, quinidines, mefloquine, halofantrine, chloroquine, amodiaquine, acridine, benzonaphthyridine, mepacrine, pyronaridine, dapsone, sulphonamide, sulfadoxine, sulfalenes, trimethoprim, proguanil, chlorproguanil, diaminopyrimidine, pyrimethamine, primaquine, aminoquinolines, clindamycin, artemisinin, dihydroartemisinin, arteether, artesunate, atovaquon, suramin, melarsoprol, nifurtimox, stibogluconate sodium, pentamidine, amphotericin B, metronidazole, clioquinol, mebendazole, niclosamide, praziquantel, pyrantel, tiabendazole, diethylcarbamazine, ivermectin, bithionol, oxamniquine, metrifonate, piperazine, and embonate.

10. The method of claim 2 wherein the composition further comprises oral cephalosporin.

11. A method of treating an infection caused by a parasite or a virus in an individual, comprising:

administering to the individual a composition comprising a pharmaceutically acceptable excipient and an effective amount of an organophosphorous compound of the general formula (1):

(I)

wherein:

R₁ and R₂ are independently selected from the group consisting of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, substituted and unsubstituted heterocyclic radical, halogen, OX₁, and OX₂, wherein X₁ and X₂ are independently selected from the group consisting of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, and substituted and unsubstituted heterocyclic radical;

A is a 2–9 carbon moiety selected from the group consisting of alkylene radical, alkenylene radical, and hydroxyalkylene radical, wherein A includes a straight chain of at least two carbon atoms between the nitrogen atom and the phosphorus atom of general formula (I);

R₃ and R₄ are independently selected from the group consisting of hydrogen, substituted and unsubstituted C$_{1-26}$-alkyl, substituted and unsubstituted hydroxy-C$_{1-26}$-alkyl, substituted and unsubstituted aryl, substituted and unsubstituted acyl, substituted and unsubstituted aralkyl, substituted and unsubstituted C$_{1-26}$-alkenyl, substituted and unsubstituted C$_{1-26}$-alkinyl, substituted and unsubstituted cycloalkyl, substituted and unsubstituted heterocyclic radical, halogen, OX₃, and OX₄, wherein X₃ and X₄ are independently selected from the group consisting of hydrogen, substituted and unsubstituted C$_{1-26}$-alkyl, substituted and unsubstituted hydroxyl-C$_{1-26}$-alkyl, substituted and unsubstituted aryl, substituted and unsubstituted aralkyl, substituted and unsubstituted C$_{1-26}$-alkenyl, substituted and unsubstituted C$_{1-26}$-alkinyl, substituted and unsubstituted cycloalkyl, substituted and unsubstituted heterocyclic radical, silyl, a metal of the first, second or third main group of the periodic table, ammonium, substituted ammonium, ammonium salt of ethylene diamine, and ammonium salt of an amino acid or an organic or inorganic acid salt thereof.

12. The method of claim 11 wherein the infection is caused by a virus and the virus is selected from the families of viruses consisting of Parvoviridae, Adenoviridae, Papovaviridae, Herpesviridae, Poxviridae, Hepadna, Picornaviridae, Calciviridae, Reoviridae, Togaviridae, Flaviviridae, Orthomyxoviridae, Parmayxoviridae, Rhabdoviridae, Coronaviridae, Bunyaviridae, Arenaviridae, Retroviridae, and Fioviridae.

13. The method of claim 11 wherein the organophosphorous compound is of the Formula (II):

(II)

wherein

X₁ is selected from the group consisting of hydrogen, substituted or unsubstituted acyl, substituted or unsubstituted alkyl, substituted or unsubstituted aryl, substituted or unsubstituted aralkyl, substituted or unsubstituted cycloalkyl, and substituted or unsubstituted heterocyclic radical.

14. The method of claim 11 wherein the infection is caused by a parasite and the infection is malaria.

15. The method of claim 11 wherein the infection is caused by a virus and the virus is selected from the group consisting of parvo viruses, dependo viruses, denso viruses, adeno viruses, mastadeno viruses, aviadeno viruses, papova viruses, papilloma viruses, JC-virus, BK-virus, miopapova viruses, herpes simplex viruses, varicella-zoster viruses, human cytomegalo virus, Epstein-Barr viruses, human herpes virus 6, human herpes virus 7, human herpes virus 8, pox viruses, orthopox, parapox, molluscum contagiosum virus, avipox viruses, capripox viruses, leporipox viruses, hepatitis viruses, hepatitis A virus, hepatitis B virus, hepatitis C viruses, hepatitis D viruses, hepatitis E viruses, hepatitis F viruses, hepatitis G viruses, hepadna viruses, picorna viruses, entero viruses, polio viruses, coxsackie viruses, echo viruses, rhino viruses, aphtho viruses, reo viruses, orbi viruses, rota viruses, toga viruses, alpha viruses, rubi viruses, pestiviruses, rubella virus, flavi viruses, Early Summer Meningoencephalitis virus, influenza viruses, paramyxo viruses, morbilli virus, pneumo virus, measles virus, mumps virus, rhabdo viruses, rabies virus, lyssa virus, Vesicula Stamatitis virus, corona viruses, bunya viruses, nairo virus, phlebo virus, uuku virus, hanta virus, hantaan virus, arena viruses, lymphocytic choriomeningitis virus, retro viruses, human T-cell leukaemia virus, oncorna viruses, spuma viruses, lenti viruses, Human immunodeficiency viruses, Marburg virus, Ebola virus, slow viruses, oncoviruses, and leukaemia viruses.

16. The method of claim 11 wherein the infection is caused by a parasite and the infection is selected from the group consisting of malaria, sleeping sickness, Chagas' disease, toxoplasmosis, amoebic dysentery, leishmaniasis, trichomoniasis, pneumocystosis, balantidiasis, cryptosporidiasis, sarcocystosis, acanthamebiasis, naegleriasis, coccidiosis, giardiasis, and lambliosis.

* * * * *